(12) United States Patent
Giera et al.

(10) Patent No.: US 6,235,937 B1
(45) Date of Patent: May 22, 2001

(54) PROCESS FOR THE PREPARATION OF NITRODIPHENYLAMINES

(75) Inventors: Henry Giera, Grosskitzighofen; Walter Lange, Odenthal, both of (DE); Torsten Pohl, Cambridge, MA (US); Adolf Sicheneder, Hohenlockstedt; Christoph Schild, Leverkusen, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/652,072

(22) Filed: Aug. 31, 2000

(30) Foreign Application Priority Data

Sep. 6, 1999 (DE) .............................................. 199 42 394

(51) Int. Cl.$^7$ ................................................ C07C 209/10
(52) U.S. Cl. .............................................................. 564/406
(58) Field of Search ............................................... 564/406

(56) References Cited

U.S. PATENT DOCUMENTS

| 2,927,943 | 3/1960 | Merz | 260/576 |
|---|---|---|---|
| 3,393,241 | 7/1968 | Nielsen | 26/576 |
| 3,435,074 | 3/1969 | Terao et al. | 260/576 |
| 4,122,118 | 10/1978 | George et al. | 260/576 |
| 4,782,185 | * 11/1988 | Muller . | |
| 5,576,460 | 11/1996 | Buchwald et al. | 564/386 |
| 5,831,128 | 11/1998 | Beller et al. | 564/405 |

FOREIGN PATENT DOCUMENTS

| 3246151 | 6/1984 | (DE) . |
|---|---|---|
| 197 38 860 | 3/1999 | (DE) . |
| 99/01418 | 1/1999 | (WO) . |

OTHER PUBLICATIONS

Journal of Organic Chemistry, Bd. 64, Nr. 15, Jul. 7, 1999, Seiten 5575–5580, XP002153304.
John F. Hartwig, et al, "Room–Temperature Palladium–Catalyzed Amination of Aryl Bromides And Chlorides And Extended Scope Of Aromatic C–N Bond Formation With A Commercial Ligand".

\* cited by examiner

Primary Examiner—Samuel Barts
(74) Attorney, Agent, or Firm—Joseph C. Gil; Noland J. Cheung

(57) ABSTRACT

The invention relates to a process for the preparation of nitrodiphenylamines by reaction of nitrohalogenobenzenes with aromatic amines in the presence of a palladium catalyst and a base, the base being ground and/or dried before its use.

6 Claims, No Drawings

PROCESS FOR THE PREPARATION OF NITRODIPHENYLAMINES

FIELD OF THE INVENTION

The invention relates to a process for the preparation of nitrodiphenylamines, in particular 4-nitrodiphenylamine (4-NDPA), by reaction of nitrohalogenobenzenes with aromatic amines in the presence of a palladium catalyst and a base.

BACKGROUND OF THE INVENTION

The preparation of nitrodiphenylamines by reaction of corresponding aromatic amines with p-nitrochlorobenzene in the presence of an acid acceptor or a neutralizing agent, optionally in the presence of a catalyst, is known and is described, for example, in DE-A 3,246,151.

The disadvantages of the processes described above are often the inadequate selectivities which, in addition to losses in yield, as a rule, necessitate more or less expensive purification steps before the nitrodiphenylamines can be reacted further, for example by hydrogenation to 4-aminodiphenylamines.

A more recent method for the preparation of arylamines by reaction of amines with aromatic compounds, for example, also halogenated nitrobenzenes, in the presence of a palladium catalyst and a base is described in U.S. Pat. No. 5,576,460. It is furthermore known from EP-A 846,676, for example, to react nitrohalogenobenzenes with aromatic amines in the presence of a palladium catalyst, a base and a halide as a co-catalyst.

WO 99/01418 describes the reaction in water with palladium catalysts and water-soluble phosphines. As a rule, the low yields of 20–50% are a disadvantage in this process.

SUMMARY OF THE INVENTION

Therefore, it was desirable to provide a process for the preparation of 4-aminodiphenylamines, which starts from aromatic amines and leads to the desired nitrodiphenylamines in good yields and high purities by reaction of corresponding p-nitrohalogenobenzenes.

The present invention therefore provides a process for the preparation of nitrodiphenylamines by reaction of nitrohalogenobenzenes with aromatic amines in the presence of a base and a palladium catalyst, wherein a palladium-phosphine complex or other palladium complexes are employed as the palladium catalyst; and alkali metal and/or alkaline earth metal carbonates, alcoholates and/or hydroxides are used as bases, the bases being ground and/or dried before their use.

DETAILED DESCRIPTION OF THE INVENTION

Nitrohalogenobenzenes which are preferably employed are those in which the nitro group is in the para-position relative to the halogen radical. Possible halogen radicals are: fluorine, chlorine, bromine and iodine, preferably chlorine and bromine. It is of course possible for the nitrohalogenobenzenes to be further substituted by other radicals, such as, for example, $C_1$–$C_4$-alkyl radicals. The nitro group can of course also be in a position relative to the halogen radicals other than the para-position, such as in the 2- and 3-position.

Nitrohalogenobenzenes, which may be mentioned are, for example: 4-nitro-2-methylchlorobenzene, 4-nitro-3-methylchlorobenzene, 4-nitrochlorobenzene, 3-nitrochlorobenzene and 2-nitrochlorobenzene. 4-Nitrochlorobenzene is particularly preferred.

Aromatic amines which can be employed in the process according to the present invention are the aromatic amines which are known for such a reaction, for example aniline, o-toluidine, m-toluidine, p-toluidine, 4-ethylaniline, 4-butylaniline, 4-isopropylaniline, 3,5-dimethylaniline and 2,4-dimethylaniline. Aniline is preferred. The aromatic amines can of course also be employed in the form of mixtures, in particular isomeric mixtures.

In the process according to the present invention, 1 to 10 mol, preferably 1.5 to 6 mol, more preferably 2 to 4 mol of the aromatic amine are in general employed per mol of nitrohalogenobenzene.

As mentioned above, catalysts which are particularly suitable for the process according to the present invention are palladium-phosphine complex compounds, where the palladium has the valency 0 or II and possible phosphine ligands are, for example, compounds such as triphenylphosphine, tri-o-toluylphosphine, tricyclohexylphosphine, tri-t-butylphosphine, bisdiphenylphosphine-ethane, bisdiphenylphosphinepropane, bisdiphenylphosphinobutane, bisdicyclohexylphosphinoethane, bisdiphenylphosphinoferrocene, 5,5'-dichloro-6,6'-dimethoxy-biphenyl-2,2'-diyl-bisdiphenylphosphine, bis-4,4'-dibenzofuran-3,3'-yl-bisdiphenylphosphine, 1,1'-bisdiphenylphosphino-diphenyl ether and bisdiphenylphosphinobinaphthyl, wherein the phenyl radicals thereof can be substituted by sulfonic acid radicals or can optionally be replaced by one or more $C_1$–$C_{12}$-alkyl groups or $C_3$–$C_{10}$-cycloalkyl groups. Polymer-bonded phosphines can furthermore also serve as ligands. Triphenylphosphine is preferably used as the ligand.

However, ligands other than the phosphine ligands mentioned can also be employed for the process according to the present invention, such as, for example, nitrogen- or oxygen-containing ligands or also ligands containing two or more different heteroatoms.

Palladium compounds which may be mentioned are, for example, the following compounds: $Pd_2dba_3$, $Pd(acac)_2$, $Pd(Oac)_2$, $PdCl_2$, $(CH_3CN)_2Pd(NO_2)Cl$ and also other palladium halides, such as bromides and iodides, acetates, carbonates, ketonates, nitrates, acetonates or palladacyclic compounds. Heterogeneous or immobilized palladium catalysts can, furthermore, also be employed in the process according to the invention. It is possible here to employ a complex which has already been prepared beforehand or to form a complex in situ from a suitable Pd compound and a ligand.

In the palladium-phosphine complexes to be employed according to the present invention, the ratio of the corresponding ligand to palladium is about 40:1 to 1:1, preferably 10:1 to 2:1, and most preferably 8:1 to 4:1.

According to the present invention, the palladium-phosphine complexes or the other complexes are in general employed in amounts of 0.0001 mol % to 10 mol %, preferably 0.001 mol % to 5 mol %, based on the nitrohalogenobenzenes employed.

Bases which are employed in the process according to the present invention are alkali metal and/or alkaline earth metal carbonates, alcoholates and/or hydroxides, potassium and/or sodium carbonate, caesium carbonate, sodium methanolate and barium hydroxide being mentioned in particular. Potassium and/or sodium carbonate are preferably employed. The bases can be employed in less than the stoichiometric amount or in an excess of up to ten times the equivalent amount with respect to the nitrohalogenobenzene. The bases are most preferably employed in amounts of 0.3 to 2 equivalents, based on the nitrohalogenobenzene.

The process according to the present invention can be carried out at temperatures in the range from 20 to 250° C., but preferably at temperatures of 120 to 180° C. The reaction temperatures here depend, in particular, on the nature of the starting substances, the catalyst and the bases employed.

The process according to the present invention can be carried out both in the presence and in the absence of a suitable solvent. Possible solvents are, for example, inert organic hydrocarbons, such as xylene and toluene. Furthermore, the aromatic amines employed can themselves function as solvents.

In the process described, the water of reaction formed can optionally be removed analogously to DE-A 2,633,811 and DE-A 3,246,151, for example by distillation with the aid of a suitable entraining agent, or this step can also be omitted.

The amount of solvents employed can easily be determined by appropriate preliminary experiments.

It is essential for the process according to the present invention that the bases employed are pretreated by grinding and/or drying.

The grinding in the process according to the present invention can be carried put, for example, in commercially available kitchen or ball mills. The grinding measure here has the effect of a drastic increase in the specific surface area, which leads to a significant increase in the conversion. In many cases, an increase in the specific surface area by a factor of 10 to 20 is to be observed by grinding. In the process described, an increase in the conversions from approx. 5 to 45% to 85 to 100% under comparable reaction conditions is achieved as a result. The increase in the specific surface area can be achieved here by grinding, precipitation or by other suitable measures.

In the process according to the present invention, an increase in the specific surface area to 0.1 to 10 $m^2/g$, preferably 0.2 to 1 $m^2/g$, is necessary to achieve higher conversions.

Investigations of the morphology demonstrate that to increase the conversions by grinding the bases, primary crystallite sizes of 20 $\mu m$ and less must be achieved.

Because of the pronounced hygroscopic properties of the bases employed in the process according to the present invention, these tend towards a greater or lesser uptake of atmospheric constituents, such as water and carbon dioxide. A significant influence on the conversions to be achieved is detectable here above an uptake of 30 percent by weight.

The bases are dried here, for example, by heating at temperatures of between 50 and 200° C., preferably between 100 and 160° C., under a reduced pressure of 0.01 to 100 mbar for several hours.

The process according to the present invention can be carried out by conventional methods in a continuous or discontinuous manner.

The corresponding nitrodiphenylamines are obtained with high selectivities (>98%) and in yields of up to 99%, depending on the amount of catalyst employed, by the process according to the present invention. The nitrodiphenylamines prepared by the process according to the present invention are obtained in particularly high purities. Other advantages over the known processes which may be mentioned are the substantially shortened reaction time of 10 minutes to about 2 hours, so that very high space/time yields can be achieved with the process according to the present invention.

The nitrodiphenylamines prepared by the process according to the present invention can be converted into the corresponding aminodiphenylamines, for example, by a hydrogenation reaction, for example, 4-aminodiphenylarnine (4-ADPA), which is an important intermediate product for the preparation of anti-aging agents and for stabilizers in the rubber and polymer industry, can be obtained by hydrogenation of 4-nitrodiphenylamine.

EXAMPLES

Example 1

Pretreatment of the bases:

By way of example, commercially available potassium carbonate is ground in a kitchen or ball mill for approx. 5 minutes. By this means, the potassium carbonate from Grüssing treated in this manner undergoes an increase in the specific surface area from 0.04 $m^2/g$ to 0.52 $m^2/g$ and achieves a primary crystallite size of 10 $\mu m$ and less. The ground potassium carbonate is subsequently dried under a pressure of 1 mbar at a temperature of 150° C. for 5 hours. If other bases are used, these are pretreated in an analogous manner.

Example 2

186 g (2 mol) aniline, 152.5 mg (0.5 mmol) palladium acetonylacetonate and 524 mg (2 mmol) triphenylphosphine are initially introduced into a three-necked round-bottomed flask under argon and are stirred at room temperature for 10 minutes. 78.5 g (0.5 mol) 4-chloronitrobenzene are added and the mixture is stirred at room temperature for a further 10 minutes. 96.6 g (0.7 mol) potassium carbonate which has been pretreated beforehand in the manner described in Example 1 are then added. The mixture is heated at 170° C. for one hour, with vigorous stirring, gas chromatography analysis of a sample after a reaction time of 0.5 hour already demonstrating complete conversion.

The mixture is allowed to cool to 70° C. and is diluted with 750 ml ethyl acetate and washed with 500 ml water. The organic phase is extracted with a solution of 100 g sodium chloride and 500 ml water and, after separation of the phases, aniline and water are removed by distillation at 70° C. 107 g (100% of theory) of a brownish solid which, according to GC analysis, having a purity of greater than 99%, are obtained.

Example 3

3.750 g (40 mmol) aniline, 3.1 mg (0.00336 mmol) palladiumdibenzylidene-acetone and 7.0 mg (0.027 mmol) triphenylphosphine are initially introduced into a three-necked round-bottomed flask under argon and the mixture is stirred at room temperature for 10 minutes. 1.055 g (6.72 mmol) 4-chloronitrobenzene are added and the mixture is stirred at room temperature for a further 10 minutes. 1.298 g (9.4 mmol) potassium carbonate which has not been pretreated in the manner described in example 1 are then added. The mixture is heated at 170° C. for one hour, with vigorous stirring. According to analysis by gas chromatography, a conversion of 48% is achieved.

Example 4

3.750 g (40 mmol) aniline, 3.1 g (0.00336 mmol) palladiumdibenzylidene-acetone and 7.0 mg (0.027 mmol)

triphenylphosphine are initially introduced into a three-necked round-bottomed flask under argon and the mixture is stirred at room temperature for 10 minutes. 1.055 g (6.72 mmol) 4-chloronitrobenzene are added and the mixture is stirred at room temperature for a further 10 minutes. 1.298 g (9.4 mmol) potassium carbonate which has been pretreated beforehand in the manner described in Example 1 are then added. The mixture is heated at 170° C. for one hour, with vigorous stirring. According to analysis by gas chromatography, a conversion of 97% is achieved.

Example 5

186 g (2 mol) aniline, 152.5 mg (0.5 mmol) palladium acetonylacetonate and 524 mg (2 mmol) triphenylphosphine are initially introduced into a three-necked round-bottomed flask under argon and the mixture is stirred at room temperature for 10 minutes. 78.5 g (0.5 mol) 4-chloronitrobenzene are added and the mixture is stirred at room temperature for a further 10 minutes. 48.3 g (0.35 mol) potassium carbonate which has been pretreated beforehand in the manner described in Example 1 are then added. The mixture is heated at 170° C. for one hour with vigorous stirring and the gas chromatography analysis of a sample after a reaction time of 0.5 hour already demonstrating complete conversion.

The mixture is allowed to cool to 70° C. and is diluted with 500 ml ethyl acetate and washed with 500 ml water. The organic phase is extracted with a solution of 100 g sodium chloride and 500 ml water and, after separation of the phases, aniline and water are removed by distillation at 70° C.

106.55 g (99% of theory) of a brownish solid which, according to GC analysis, has a purity of 99% are obtained.

Example 6

186 g (2 mol) aniline, 152.5 mg (0.5 mmol) palladium acetonylacetonate and 623 mg (1 mmol) 2,2'-bis-(diphenylphosphino)-1,1'-binaphthyl are initially introduced into a three-necked round-bottomed flask under argon and the mixture is stirred at room temperature for 10 minutes. 78.5 g (0.5 mol) 4-chloronitrobenzene are added and the mixture is stirred at room temperature for a further 10 minutes. 96.6 g (0.7 mol) potassium carbonate which has been pretreated beforehand in the manner described in Example 1 are then added. The mixture is heated at 170° C. for one hour, with vigorous stirring, gas chromatography analysis of a sample after a reaction time of 0.5 hour already demonstrating complete conversion.

Example 7

18.6 g (0.2 mol) aniline, 15.3 mg (0.05 mmol) palladium acetonylacetonate and 53.8 mg (0.1 mmol) bis-(2-diphenylphosphino)-phenyl ether are initially introduced into a three-necked round-bottomed flask under argon and the mixture is stirred at room temperature for 10 minutes. 7.85 g (0.05 mol) 4-chloronitrobenzene are added and the mixture is stirred at room temperature for a further 10 minutes. 9.66 g (0.07 mol) potassium carbonate which has been pretreated beforehand in the manner described in Example 1 are then added. The mixture is heated at 170° C. for one hour, with vigorous stirring, gas chromatography analysis of a sample after a reaction time of 0.5 hour demonstrating a conversion of 99%.

Example 8

9.376 g (0.1 mol) aniline, 7.6 mg (0.0083 mmol) palladiumbenzylidene-acetone and 17.6 mg (0.067 mmol) triphenylphosphine are initially introduced into a three-necked round-bottomed flask under argon and the mixture is stirred at room temperature for 10 minutes. 2.64 g (0.0168 mol) 4-chloronitrobenzene are added and the mixture is stirred at room temperature for a further 10 minutes. 2.502 g (0.0236 mol) sodium carbonate which has been pretreated beforehand in the manner described in example 1 are then added. The mixture is heated at 175° C. for one hour, with vigorous stirring. According to analysis by gas chromatography, a conversion of 74% is achieved.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of nitrodiphenylamines by reacting nitrohalogenobenzenes with aromatic amines in the presence of a base and a palladium catalyst, wherein said palladium catalyst comprises a palladium-phosphine complex or other palladium complexes and said bases comprise alkali metal and/or alkaline earth metal carboxylates, alcoholates and/or hydroxides, wherein said bases are ground and/or dried before their use.

2. A process according to claim 1, wherein said nitrohalogen benzene is selected from the group consisting of 4-nitro-2-methylchlorobenzene, 4-nitro-3-methylchlorobenzene, 4-nitrochlorobenzene, 3-nitrochlorobenzene and 2-nitrochlorobenzene.

3. A process according to claim 2, wherein said nitrohalogen benzene is 4-nitrochlorobenzene.

4. A process according to claim 1, wherein said aromatic amine is selected from the group consisting of aniline, o-toluidine, m-toluidine, p-toluidine, 4-ethylaniline, 4-butylaniline, 4-isopropylaniline, 3,5-dimethylaniline and 2,4-dimethylanline.

5. A process according to claim 4, wherein said aromatic amine is aniline.

6. A process according to claim 1, wherein said nitrodiphenylamine is 4-nitrodiphenylamine.

* * * * *